(12) United States Patent  (10) Patent No.: US 7,470,917 B1
Hoang et al.  (45) Date of Patent: Dec. 30, 2008

(54) SUBMERSIBLE APPARATUS FOR MEASURING ACTIVE FLUORESCENCE

(75) Inventors: Sang Hoang, Campbell, CA (US);
James Crawford, Los Gatos, CA (US);
David Doting, Morgan Hill, CA (US);
Sorin Florea, San Jose, CA (US);
Steven Monsef, Los Gatos, CA (US);
Frank Szcurko, Belmont, CA (US)

(73) Assignee: Turner Designs, Inc., Sunnyvale, CA (US)

( * ) Notice: Subject to any disclaimer, the term of this patent is extended or adjusted under 35 U.S.C. 154(b) by 219 days.

(21) Appl. No.: 11/422,064

(22) Filed: Jun. 2, 2006

Related U.S. Application Data

(63) Continuation-in-part of application No. 11/303,446, filed on Dec. 15, 2005, now Pat. No. 7,301,158.

(60) Provisional application No. 60/637,478, filed on Dec. 15, 2004.

(51) Int. Cl.
*G01J 1/58* (2006.01)
(52) U.S. Cl. .................................. 250/458.1
(58) Field of Classification Search ............... 250/458.1
See application file for complete search history.

(56) References Cited

U.S. PATENT DOCUMENTS

| | | | |
|---|---|---|---|
| 4,293,225 A | 10/1981 | Wheaton et al. | |
| 4,553,034 A | 11/1985 | Byers et al. | |
| 4,637,719 A * | 1/1987 | Herman | 356/72 |
| 4,650,336 A | 3/1987 | Moll | |
| 4,652,143 A | 3/1987 | Wickersheim et al. | |
| 4,750,837 A | 6/1988 | Gifford et al. | |
| 4,802,768 A | 2/1989 | Gifford et al. | |
| 4,804,850 A | 2/1989 | Norrish et al. | |
| 4,942,303 A * | 7/1990 | Kolber et al. | 250/458.1 |
| 5,350,922 A | 9/1994 | Bartz | |
| 5,418,614 A | 5/1995 | Brost et al. | |
| 5,424,840 A * | 6/1995 | Moore et al. | 356/410 |
| 5,426,306 A | 6/1995 | Kolber et al. | |
| 6,121,053 A | 9/2000 | Kolber et al. | |
| 6,255,118 B1 | 7/2001 | Alfano et al. | |
| 6,277,330 B1 | 8/2001 | Liu et al. | |
| 6,307,630 B1 | 10/2001 | Banerjee | |
| 6,369,894 B1 | 4/2002 | Rasimas et al. | |
| 6,407,383 B1 | 6/2002 | Byatt et al. | |
| 6,525,325 B1 | 2/2003 | Andrews et al. | |
| 6,563,122 B1 | 5/2003 | Ludeker et al. | |
| 6,836,325 B2 | 12/2004 | Maczura et al. | |
| 7,099,012 B1 | 8/2006 | Crawford et al. | |
| 7,301,158 B1 | 11/2007 | Hoang | |
| 2003/0048445 A1* | 3/2003 | Tokhtuev et al. | 356/411 |
| 2004/0179196 A1* | 9/2004 | Hart | 356/318 |

* cited by examiner

*Primary Examiner*—David P Porta
*Assistant Examiner*—Mark R Gaworecki
(74) *Attorney, Agent, or Firm*—Adeli & Tollen LLP

(57) ABSTRACT

A submersible fluorometer for measuring a fluorescence of a photosynthetic material in a liquid, the fluorometer includes a set of light emitting diodes (LEDs) for supplying light to direct towards the liquid and a photodiode for measuring a detected light emitted from the liquid. The light is used for measuring the fluorescence of the photosynthetic material in the liquid. The fluorometer also has a water-tight volume for protecting the photodiode from the liquid.

32 Claims, 9 Drawing Sheets

SUBMERSIBLE APPARATUS FOR MEASURING ACTIVE FLUORESCENCE

RELATED APPLICATIONS

This patent application is a continuation-in-part of the U.S. patent application entitled "Method and Apparatus for measuring active fluorescence" having Ser. No. 11/303,446 filed on Dec. 15, 2005 now U.S. Pat. No. 7,301,158, which claims the benefit of the previous U.S. Provisional Application 60/637,478, entitled "Method and Apparatus for measuring active fluorescence", filed Dec. 15, 2004. Both these applications are incorporated herein by reference.

BACKGROUND OF THE INVENTION

The use of fluorescence to measure the photosynthetic activity of organisms has been an accepted method in the scientific community for many years. Measuring fluorescence as a function of photosynthetic activity, compared to other methodologies, is fast, easy to use, and requires relatively low cost instrumentation. The majority of fluorometers in use today are classified as passive fluorometers and are used to measure the total biomass of photosynthetic organisms. Passive fluorometers supply a constant source of light of a specific wavelength and measure the light output from the sample at a different, typically longer, wavelength. In order to measure sample levels as low as possible, passive fluorometers typically use as bright a light as possible.

A known drawback to using passive fluorescence is that the fluorescent output of a sample can vary due to several influences not related to biomass of the photosynthetic organisms. For example, an organism's fluorescent light output will vary depending on the ambient light condition of its environment. In addition, the source light used by the fluorometer can affect the organism being measured.

Active fluorescence overcomes these issues by using flash stimulated fluorescence. An example of active fluorescence is disclosed in Moll, U.S. Pat. No. 4,650,336. Moll describes a method and device to measure photosynthetic activity using variable fluorescence. Moll uses one lamp to provide constant-level light to bring about continuous, steady state fluorescence of a plant, and a flash lamp to provide a flash of light to bring about a transient fluorescence of the plant.

Another active fluorescence technique is described in Kolber et al., U.S. Pat. No. 4,942,303 ("Kolber I"). Kolber I describes a "pump and probe" technique that uses a low intensity "probe" flash to measure fluorescence before and after a bright "pump" flash to measure the change in fluorescence.

Another active fluorescence technique is described in Kolber et al., U.S. Pat. No. 5,426,306 ("Kolber II"). This technique, known as fast repetition fluorescence, uses a series of fast, repetitive flashes at controlled energies to incrementally effect photosynthetic processes.

Another active fluorescence technique is described in Kolber et al., U.S. Pat. No. 6,121,053 ("Kolber III"). Kolber III describes a multiple protocol fluorometer which allows a significant amount of control over the duration, frequency, and power of the flashes.

Previously, as can be seen in the references, fluorometers have provided researchers with progressively more control over the active fluorescence protocol. Such fluorometers provide detailed information of the photosynthetic process. This has led to the development of increasingly complex and costly instruments. With limited research budgets, many researchers cannot afford the instruments currently available.

The components used by current active fluorometers are one reason for their high costs. The current active fluorometers use bright light sources due to the weak fluorescent response of algae in water as compared to solid samples (e.g., a leaf). Using a bright light helps maximize the response to improve detection limits. Bright light sources such as the flash lamps used in Kolber I and Kolber II require a large amount of energy to work properly, and require expensive support circuitry to supply the currents they need. Moving to solid state LEDs as used in Kolber III is a step in the right direction, since LEDs require less power and less support circuitry. However, Kolber III uses a large array of LEDs driven above their nominal currents, again requiring a significant amount of energy.

Another source of large material cost is the detector for measuring the light emitted by the sample. Because the emitted light is relatively dim for algae in water, the photodetector in the above references has been a photomultiplier tube ("PMT"). A PMT is a vacuum tube with special elements to convert a detected photon to an electrical current which is then amplified internally before being provided to outside circuitry for further signal processing. PMTs are inherently expensive due to their specialized nature, many are built by hand. In addition, they require high voltage sources to operate (e.g., up to 1000 volts) which can also be expensive. Due to their construction, PMTs are fairly fragile. Not only are they encased in glass under vacuum, but the internal elements are small metal plates that are carefully aligned. PMTs therefore do not handle shock very well. In addition, PMTs are typically physically large. This makes it difficult to place them near the sample. Kolber II uses optics such as lenses and collimators to collect emission light from the sample and provide it to the PMT, again increasing components, complexity, and cost.

Further costs have been added due to the emphasis on increasing control, data acquisition, and data analysis to calculate the many parameters of photosynthesis. This requires the use of more powerful, and hence more costly, internal computers. The light sources, detectors, and computers of the current designs are all large and require a significant amount of power. This leads to large enclosures and large power sources, again increasing costs.

In addition to limited or decreasing budgets, researchers often deploy multiple sensors in situ in various locations collecting data in real time to give a broader view of the health of a body of water. Often these instruments are deployed in multiple fixed locations (e.g., a pier) and are left unattended to operate for significant periods of time (e.g., one month). An ideal instrument would have a low enough cost to allow the purchase of multiple units, would have low enough power consumption to operate on a battery for the necessary period of time, and would be submersible. In addition, many studies only require the information that can be provided by a basic active fluorometer. Therefore, there is a need in the art for a small, low cost, low power, submersible, and reliable active fluorometer.

SUMMARY OF THE INVENTION

Some embodiments of the invention provide a submersible apparatus for measuring active fluorescence in liquid samples by using solid-state components. The use of solid-state devices dramatically lowers the cost, size, and power consumption of active fluorescence while improving the ruggedness and reliability. The smaller size of the solid-state devices allows them to be placed very close to the sample. This maximizes the amount of light the sample receives from the light sources and allows efficient collection of the resulting emitted light using simple and low cost optical components.

In some embodiments, the apparatus (1) uses either a single LED or a few LEDs (4 or fewer) that are modulated to provide a measuring light source and (2) uses a small number of LEDs (12 or fewer) to provide a saturating light source. Also, the apparatus includes a photodetector that is a photodiode. The apparatus includes amplification circuitry associated with this photodiode. This amplification circuitry is synchronized to both the modulating light source and the analog to digital conversion. The apparatus in some embodiments further includes a small, low power microcontroller to control the light sources and to read, report, and/or record the output from the photodiode and its associated circuitry.

In some embodiments, the apparatus includes a sample chamber open to the liquid in which the apparatus is submerged and a photodiode for measuring a light from the sample chamber. Such embodiments have a transparent region of the sample chamber for allowing light to reach the photodiode. Such embodiments also have a set of light emitting diodes (LEDs) for supplying light to the sample chamber.

BRIEF DESCRIPTION OF THE DRAWINGS

The novel features of the invention are set forth in the appended claims. However, for purpose of explanation, several embodiments of the invention are set forth in the following figures.

DETAILED DESCRIPTION OF THE INVENTION

In the following description, numerous details are set forth for purpose of explanation. However, one of ordinary skill in the art will realize that the invention may be practiced without the use of these specific details. In other instances, well-known structures and devices are shown in block diagram form in order not to obscure the description of the invention with the unnecessary detail.

I. Mechanical and Optical Configuration

Figure 1:
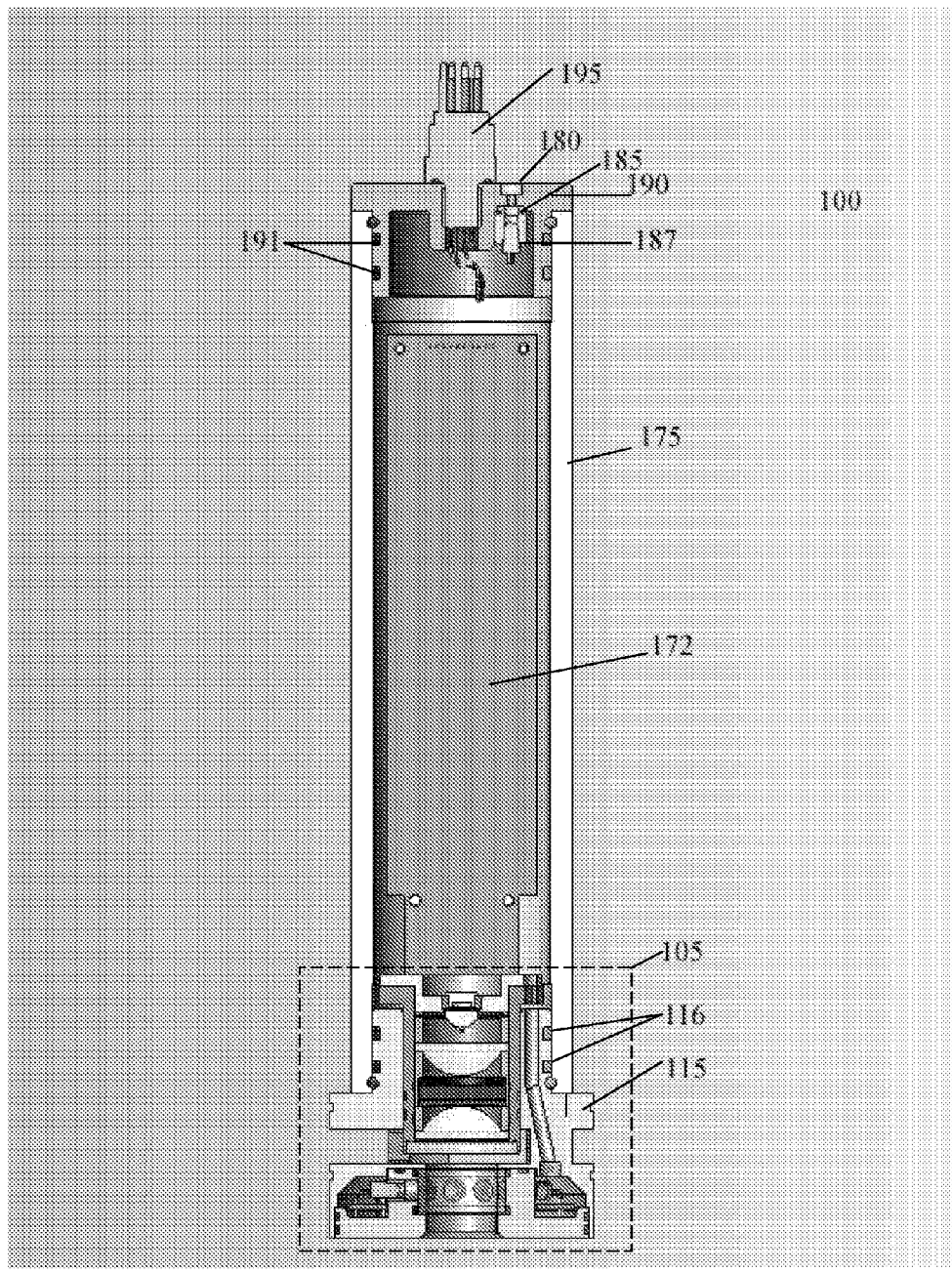
FIG. 1 illustrates cross-sectional view of the components of the fluorometer.

FIG. 1 conceptually illustrates a cross-sectional view of a submersible active fluorometer 100 of some embodiments of the invention. The submersible fluorometer can be submersed in water without damaging it. The fluorometer 100 includes optical components 105, an optical head 115, o-rings 116 and 191, a printed circuit board (PCB) 172, a tube 175, clear optical epoxy 180, a light pipe 185, a power indicator light emitting diode (LED) 187, an endcap 190, and a connector 195.

The optical components 105 are housed in optical head 115. Tube 175 forms the main housing of the fluorometer. Optical head 115 slides into tube 175 using o-rings 116 to form a water tight seal. Inside tube 175 and connected to optical components 105 is the PCB 172 containing all the necessary electronics needed to control submersible active fluorometer 100 and to communicate externally through connector 195. Connector 195 is screwed into endcap 190 which slides into tube 175 using o-rings 191 to form a water tight seal. Power indicator LED 187 connects to and is controlled by the circuitry contained on PCB 172. Light pipe 185 provides a path for the light from power indicator LED 187 to reach outside while providing an initial seal. Clear optical epoxy 180 is then used to provide the final seal and allows light from light pipe 185 to be seen. The power indicator LED 187 with its attendant light pipe 185 and clear optical epoxy 180 are found in the illustrated embodiments, but other embodiments function without them.

Figure 2:
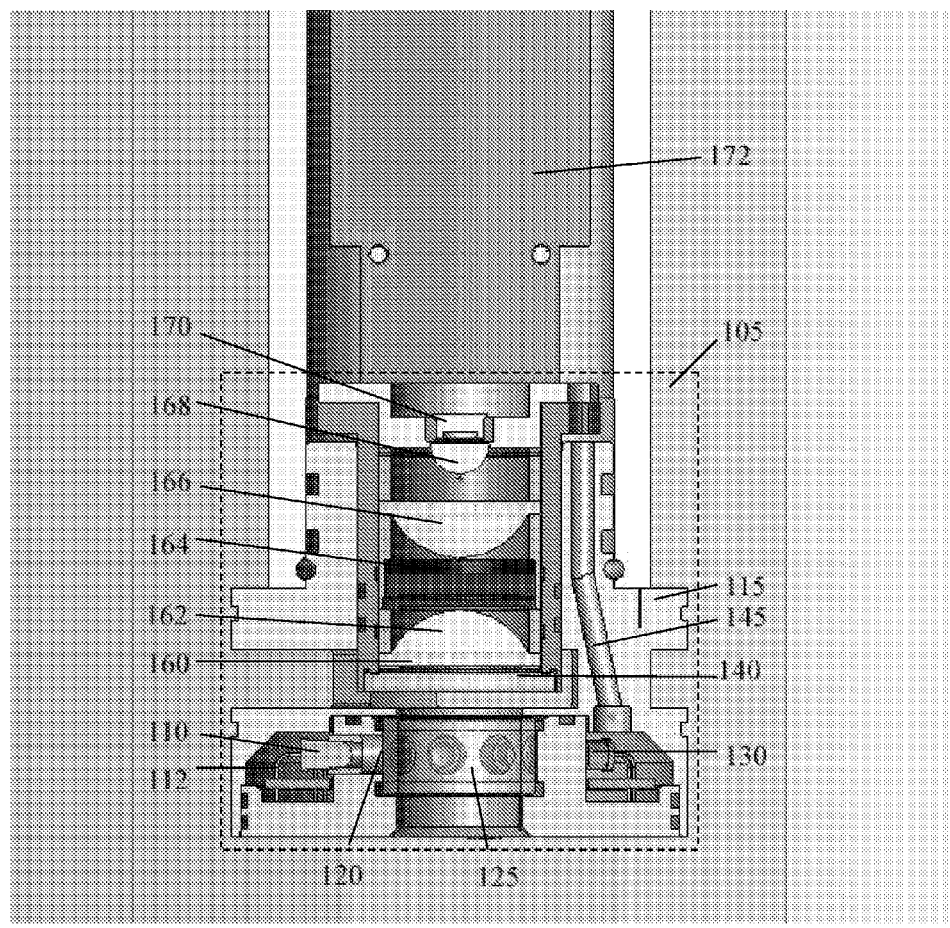
FIG. 2 illustrates the cross-sectional view of the optical components of the fluorometer.

FIG. 2 conceptually illustrates a cross-sectional view of optical components 105 of some embodiments. These components include one or more sampling LEDs 110, printed circuit board (PCB) 112, optical head 115, one or more filters 120, LED holder 125, one or more saturating LEDs 130, window 140, conduit 145, aperture 160, lenses 162, 166, and 168, emission filter 164, and photodiode 170.

LED holder 125 is a ring which will hold sampling LED(s) 110, saturating LED(s) 130, and excitation filter(s) 120. Samples in the inner volume of LED holder 125 are illuminated by the sampling LED(s) 110 and saturating LED(s) 130, which are described further below. Fluorescent light from the samples pass through the window 140. Aperture 160, just above window 140, narrows the field of view of lens 162 to the sample area within LED holder 125 and reduces the viewing of any extraneous light. The light is collimated by lens 162. The light is collimated so that it will travel orthogonally to the emission filter 164. Some emission filters 164 will not properly filter light that is not orthogonal; embodiments with such filters function better with collimated light. The light passes through the emission filter 164 which allows only the light of interest to reach photodiode 170. The light is then focused by lenses 166 and 168 onto the relatively small surface area of photodiode 170. Photodiode 170 is positioned such that it is looking into the sample area formed by the inside of LED holder 125, orthogonal to light being emitted by sampling LED(s) 110 and saturating LED(s) 130. Photodiode 170 converts the light signal into an electrical signal which is passed to the PCB 172.

The sampling and saturating LEDs are arranged axially by LED holder 125, evenly illuminating the sample volume. In embodiments with filter(s) 120, the filter(s) provide better performance by filtering the light provided by sampling LED(s) 110 and/or saturating LED(s) 130, however other embodiments function without having filter(s) 120. While filters are optional for both saturating and sampling LEDs, it is more important to have precise wavelengths (provided by filtering) from the sampling LEDs 110 than the saturating LEDs 130. This is because the sampling LEDs purpose is to provide the excitation light needed to measure fluorescence, while the function of the saturating LEDs 130 is to provide a large amount of light to induce the photosensitive life in the water to provide maximum fluorescence.

Sampling LED(s) 110 and saturating LED(s) 130 connect to printed circuit board (PCB) 112. PCB 112 provides power to sampling LED(s) 110 and saturating LED(s) 130 under control of the circuitry contained on PCB 172. PCB 172 is connected to PCB 112 with wires (not shown for clarity) that are routed through conduit 145 which is a conduit in optical head 115. This conduit may be made by drilling into optical head 115, by molding or casting of the optical head to include the conduit or by some other process.

The embodiments illustrated in the figures use different sets of LEDs for generating sampling light and saturating light. Other embodiments could use a single set of LEDs for both functions by varying the amount of power supplied to the LEDs. Lenses 168, 166, and 162 and aperture 160 are optional, but embodiments with them may provide more sensitivity by collecting light from the sample more efficiently than if they weren't present.

Figure 3:
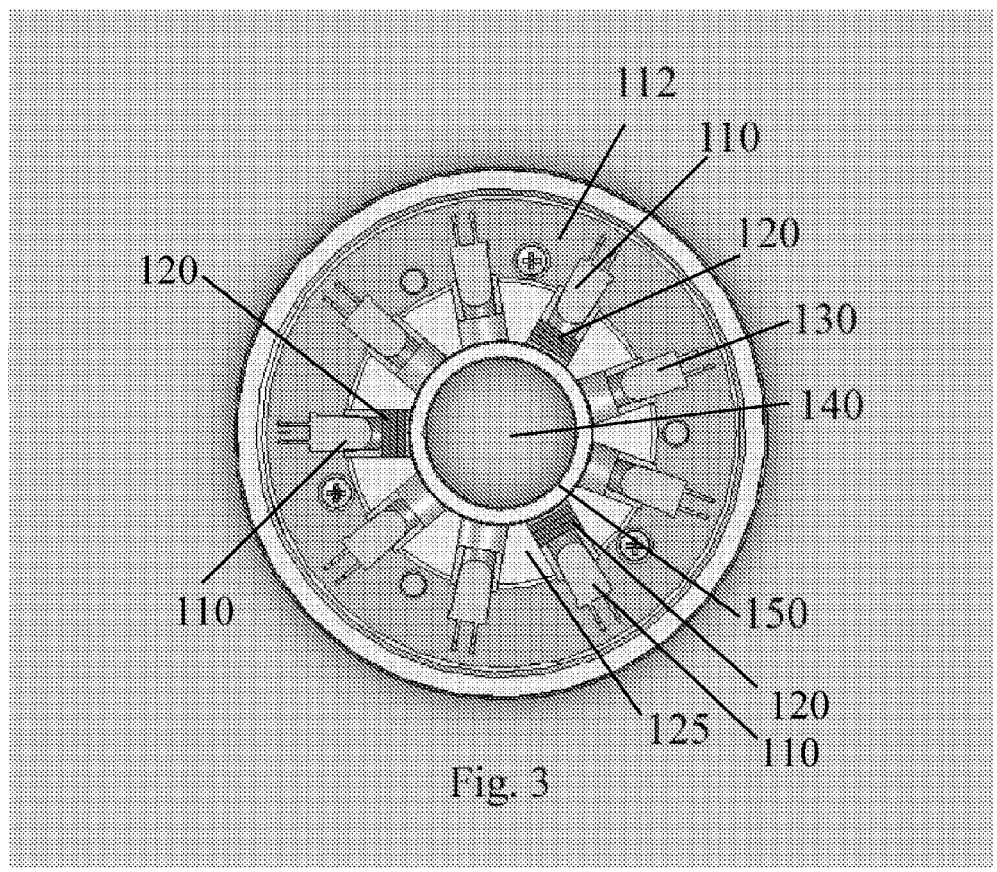
FIG. 3 illustrates another cross-sectional view of the optical components of the fluorometer.

FIG. 3 conceptually illustrates another cross-sectional view of optical components 105. In addition to components previously described, FIG. 3 includes sample tube 150. Sample tube 150 is a clear tube that fits within LED holder 125. Sample tube 150 provides a seal between the ambient water and the holes in LED holder 125 into which are inserted optional excitation filter(s) 120, sampling LED(s) 110, and saturating LED(s) 130. It is a clear tube since light from sampling LED(s) 110 and saturating LED(s) 130 must pass through it to the water contained within sample tube 150.

FIG. 3 presents a view from the bottom of active fluorometer 100 looking up towards window 140 through the sample chamber formed by the inner volume of LED holder 125. This view shows three sampling LEDs 110 arranged by LED holder 125 in a circular arrangement one-hundred-twenty degrees apart and 6 saturating LEDs 130 placed between sampling LEDs 110. The saturating LEDs 130 are forty degrees apart, from one another or the nearest sampling LED 110. Thus all LEDs are arranged symmetrically around the sample volume and provide even illumination. The actual number of sampling LEDs 110 and saturating LEDs 130 may be different in different embodiments. FIG. 3 illustrates an embodiment where excitation filters 120 are in place for sampling LEDs 110 but not for saturating LEDs 130.

It should be noted that in some embodiments, the inner volume of the LED holder (also referred to as a sample chamber) is open to the liquid in which the fluorometer is submerged. Some embodiments have multiple openings to allow water to flow into the sample chamber and any air in the chamber to flow out.

II. Circuitry for Active Fluorometer

Figure 4:
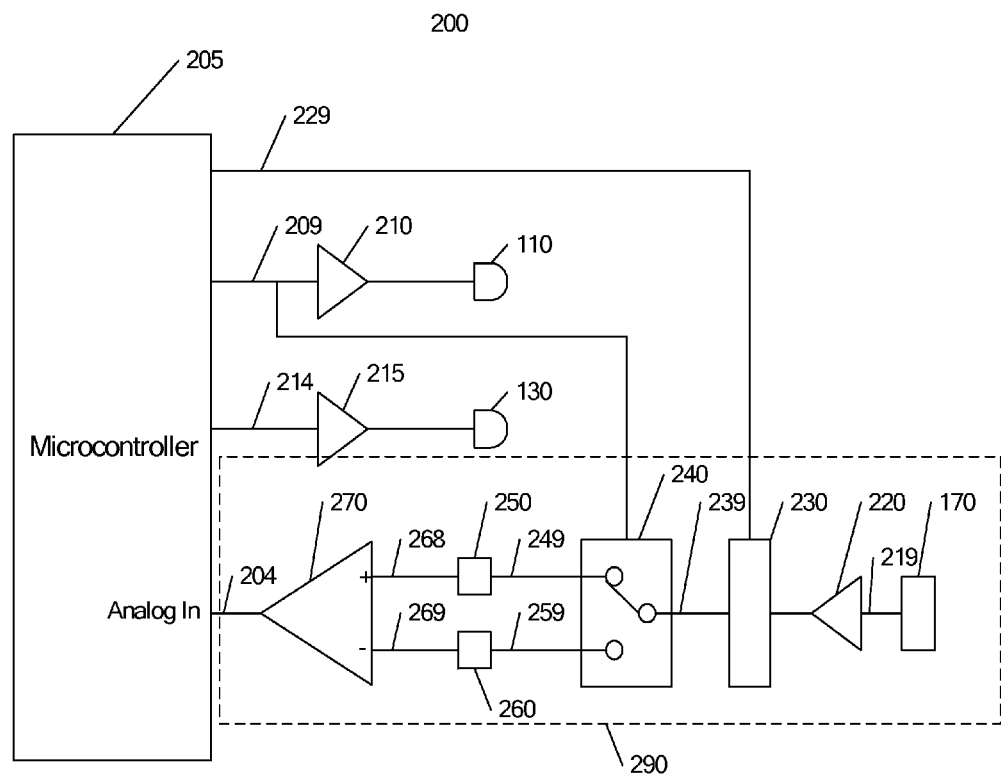
FIG. 4 illustrates a block diagram of the electronic components of the fluorometer.

FIG. 4 conceptually illustrates the electronic control system 200 of the fluorometer of some embodiments. This control system includes a microcontroller 205, a sampling LED drive circuit 210, a saturation LED drive circuit 215, an amplifier 220, a gain control circuit 230, an analog switch 240, a first hold circuit 250, a second hold circuit 260, and a differential amplifier 270 and a detection circuit 290.

The microcontroller 205 is for driving the sampling LED 110 and saturating LED 130, and processing signals from the photodiode 170. In some embodiments, the microcontroller 205 is a commercially available low cost microcontroller that includes a processor, a memory, digital inputs and outputs, an analog to digital converter, and a communicator for communicating with an external computer. While there are many low cost commercially available microcontrollers, some embodiments may use a dedicated microcontroller that is specifically designed for the fluorometer.

The microcontroller 205 is responsible for supplying signals that determine (1) when the sampling LED 110 turns on and off, (2) when the saturating LED 130 turn on and off, (3) what gain should be selected by the gain control circuit 230, etc. The gain control circuit 230 will be further described below. A digital signal 209 from the microcontroller 205 controls the sampling LED drive circuit 210. Similarly, a digital signal 214 from the microcontroller 205 controls the saturating LED drive circuit 215. The LED drive circuits 210 and 215 are designed to supply a precise amount of current to the sampling LED 110 and saturating LED 130 respectively, and to turn on and off the sampling LED 110 and saturating LED 130 very quickly.

In some embodiments, detection circuit 290 (illustrated in more detail in FIG. 5) includes, the photodiode 170 that supplies a small signal 219 to the amplifier 220 which boosts the small signal 219 to a larger value. The output of the amplifier 220 goes to the gain control circuit 230. The gain control circuit 230 is controlled by a digital signal 229 from the microcontroller 205. The purpose of gain control circuit 230 is to further amplify the output of the amplifier 220 if needed so that the signal is at a level which can be read by the analog input of the microcontroller 205. If the output signal of the amplifier 220 is small, then additional gain would be selected. If the output signal of the amplifier 220 is large, then no additional gain would be needed.

The output signal 239 from the gain control circuit 230 goes to the analog switch 240. The analog switch 240 is controlled by the same signal 209 which drives the sampling LED circuit 210. By switching in this manner, the output signal 249 of the analog switch 240 will always present the signal from the photodiode 170 when the sampling LED 110 is on. Likewise, the output signal 259 of the analog switch 240 will always present the signal from the photodiode 170 when the sample LED 110 is off. The hold circuits 250 and 260 are needed to hold the signal levels of the output signals 249 and 259 respectively, since the output signals 249 and 259 are not constantly present due to the continuous switching of the analog switch 240. The hold circuit 250 will hold the amplified signal from the photodiode 170 when the sampling LED 110 is on. The hold circuit 260 will hold the amplified signal from the photodiode 170 when the sampling LED 110 is off.

The output signal 268 of the hold circuit 250 becomes the signal to the positive input of the differential amplifier 270. The output signal 269 of the hold circuit 250 becomes the signal to the negative input of the differential amplifier 270. The output signal 204 of the differential amplifier 270 is the amplified difference between the output signals 268 and 269.

Thus the fluorometer of these embodiments measures the effect of the sampling LED 110 by subtracting out the level of light found when the sampling LED 110 is off. In some embodiments, the differential amplifier 270 is used to perform ambient light rejection. Ambient light is light in the sample's environment that is not a function of fluorescence. As such, it is an unwanted background signal. By measuring the output of the photodiode 170 when the sampling LED 110 is off, the ambient light is determined and subtracted from the measured light when the sampling LED 110 is on, thus providing a measure of fluorescence which is not affected by background illumination (e.g., ambient light). In some embodiments, where measurements are taken while the saturating LED 130 is turned on, the differential amplifier also serves to reject that portion of the fluorescence that is caused by the saturating LED 130 and not by the sampling LED 110. An analog to digital circuitry contained in the microcontroller 205 uses the output signal 204 from the differential amplifier 270 and converts it to a digital value which is then communicated externally. In some embodiments, the microcontroller 205 takes multiple samples during each cycle of the output signal 204 and averages them to reduce signal noise. The end result is a produced digital value that is more accurate.

In some embodiments, some functions (e.g., analog to digital converter) of the microcontroller 205 could be incorporated as a separate circuit. Furthermore, in some embodiments, some circuits (e.g., differential amplifier 270) described could also be incorporated in the microcontroller 205. Where some of the circuits are incorporated in the control system 200 is simply a design choice involving cost, size, accuracy and other factors typical in electrical system design.

Figure 5:
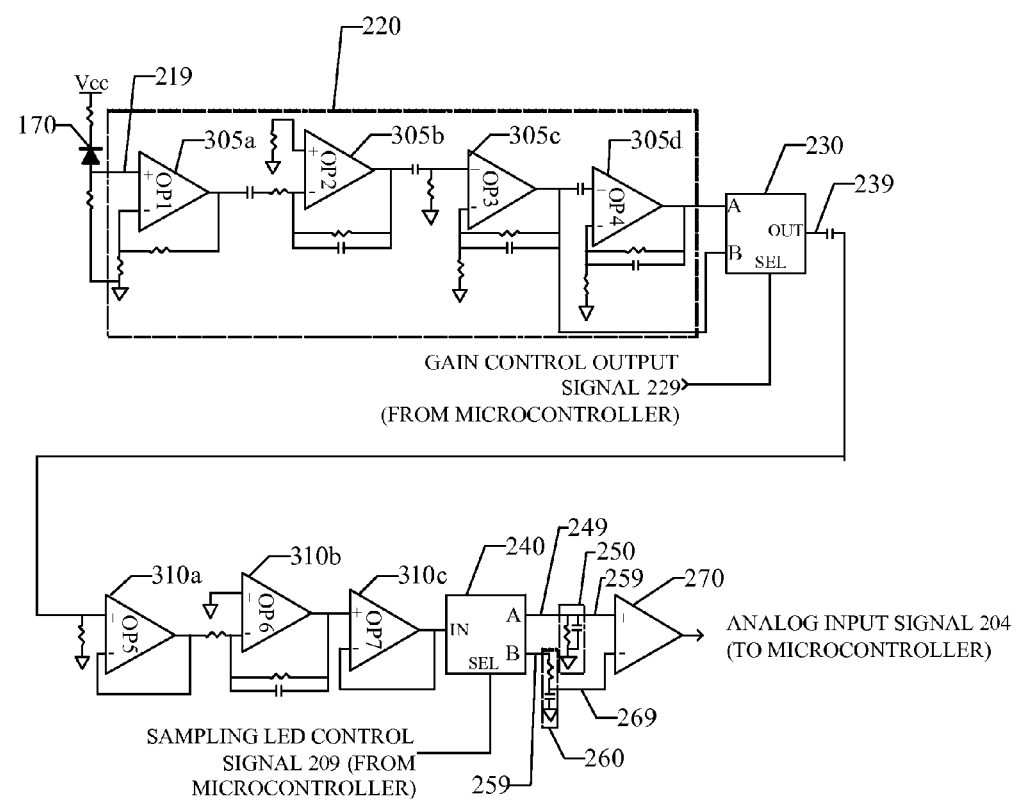
FIG. 5 illustrates a schematic of the detection circuit of the fluorometer.

FIG. 5 describes in more detail the detection circuitry 290 of some embodiments of the invention. The detection circuitry includes, photodiode 170, operational amplifiers 305a-305d (collectively operational amplifiers 305) and 310a-310c (collectively operational amplifiers 310), gain control circuit 230, gain control output signal 229, output signal 239, analog switch 240, sampling LED control signal 209, output signal 249, "on" hold circuit 250, "off" hold circuit 260, output signal 259, differential amplifier 270, output signal 269, analog input signal 204 and several resistors and capacitors, whose values are selected to provide the desired gains for the particular operational amplifiers.

Photodiode 170 supplies a small signal to the input of operational amplifier 305a. Operational amplifiers 305a through 305d (collectively operational amplifiers 305) and their associated resistors and capacitors form amplifier 220 to provide the amplification necessary to detect the signal. Operational amplifier 305a converts the current output of photodiode 170 to a voltage. Operational amplifiers 305b through 305d each provide amplification of the signal using their associated resistors while simultaneously providing some filtering of unwanted noise using their associated capacitors. This use of cascading amplification and filtering provides a much cleaner signal than a single, larger amplifier.

The output of amplifier 220 feeds into gain control circuit 230. Gain control circuit 230 can select between two levels of amplification provided by amplifier 220. The selection of the level of amplification is done by the microcontroller using gain control output signal 229. Note that there could be more than two levels of amplification selection if needed.

Output signal 239 from gain control circuit 230 goes through operational amplifiers 310a through 310c (collectively operational amplifiers 310). Operational amplifiers 310a through 310c buffer the signal between gain control circuit 230 and analog switch 240 while simultaneously filtering out noise that may have been introduced by gain control circuit 230.

Analog switch 240 is controlled by sampling LED control signal 209 provided by the microcontroller. Sampling LED control signal 209 also controls the flashing of sampling LED circuit 210 (not shown in this figure). Analog switch 240 will select one of two possible output signals. Output signal 249 will be selected when sampling LED 110 is on, output signal 259 will be selected when sampling LED 110 is off.

A resistor and capacitor network form the "on" hold circuit 250 for the signal when sampling LED 110 is on. Similarly, a resistor and capacitor network form the "off" hold circuit 260 for the signal when sampling LED 110 is off. The output signal 259 of the "on" hold circuit 250 is connected to the positive input of differential amplifier 270. The output signal 269 of the "off" hold circuit 260 is connected to the negative input of differential amplifier 270. Resulting analog input signal 204 is a signal that is proportional to the fluorescence of the sample.

III. Timing of Circuitry

Figure 6:
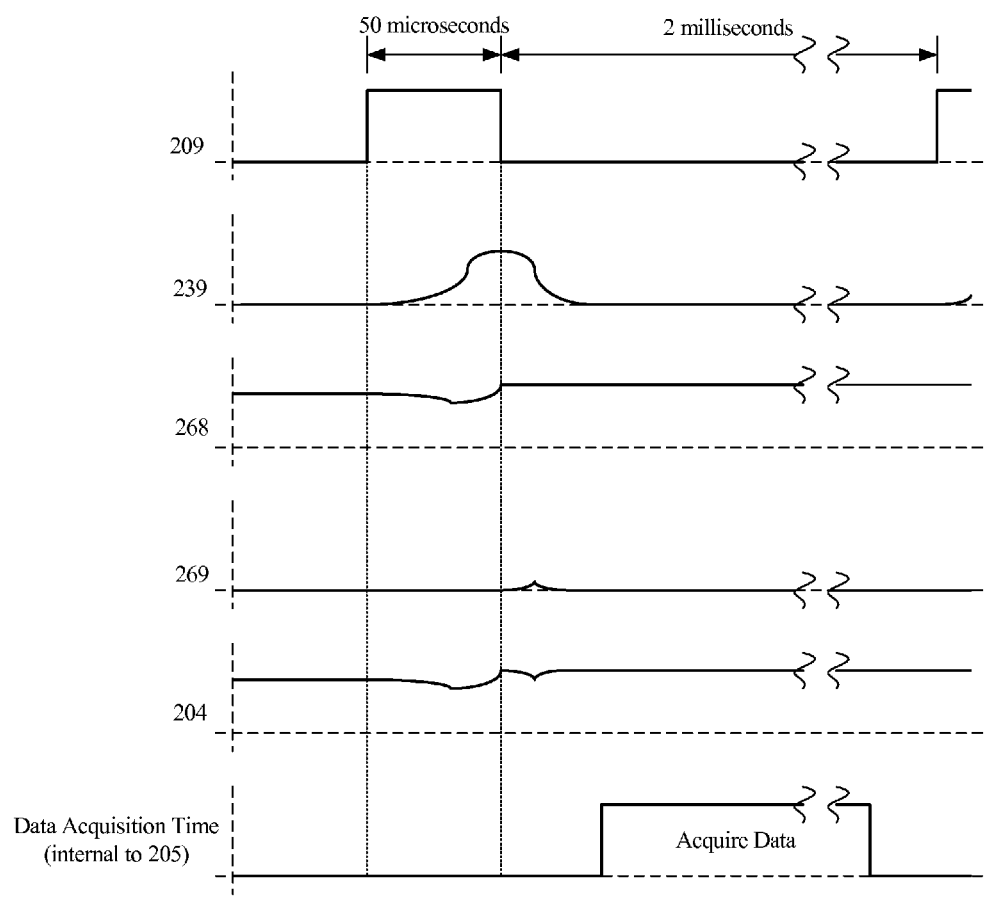
FIG. 6 illustrates a graph of the timing of the sampling LED and the measuring electronic components.

FIG. 6 illustrates a timing diagram of the detection circuit 290 in some embodiment of the invention. In an active fluorescent circuit, the sampling LED 110 ideally should not affect the sample. In other words, turning on the sampling LED 110 should not change the steady state fluorescence of the sample. In order to achieve this, the sampling LED 110 should be on for as little time as possible while still allowing the detection circuit enough time to distinguish the fluorescent signal. Thus, the sampling LED control signal 209 has a very short "on" time for the sampling LED 110.

As shown in FIG. 6, the sampling LED control signal 209 is on for 50 microseconds and off for 2 milliseconds, in some embodiments. However, other embodiments have on and off times that may vary according to various conditions. As illustrated in FIG. 6, the "on" time is significantly shorter than the "off" time.

In some embodiments, the gain control output signal 239 is an analog signal showing the detection of the fluorescent signal by the photodiode 170 above the ambient light. As shown in FIG. 6, the gain control output signal 239 will start to rise as the sampling LED 110 is turned on by the sampling LED control signal 209 and reaches its maximum before the sampling LED 110 is turned off. As further shown in this figure, the gain control output signal 239 returns to the ambient light reading when the sampling LED control signal 209 turns the sampling LED 110 off.

In some embodiments, the gain control output signal 239 is the input signal to the analog switch 240. The analog switch 240 is switched using the same sampling LED control signal 209 that controls the sampling LED 110. This means that the output signal 249 of analog switch 240 will only see the gain control output signal 239 when the sampling LED 110 is on. Likewise the output signal 259 of the analog switch 240 will only see the gain control output signal 239 when the sampling LED 110 is off. As mentioned above, these signal levels will be held by the hold circuits 250 and 260 respectively. As shown in FIG. 6, the "on" hold output signal 268 is a signal that is higher than the "off" hold output signal 269. Both the hold output signals 269 and 269 are very slow varying signals (i.e., they will not change significantly from cycle to cycle).

As previously described, the "on" hold output signal 268 becomes the positive input signal to the differential amplifier 270, while the "off" hold output signal 269 becomes the negative input signal. The differential amplifier 270 outputs the analog input signal 204, which is proportional to the difference between the hold output signals 268 and 269. In some embodiments, the microcontroller 205 will start sampling the analog input signal 204 about 100 microseconds after the sampling LED control signal 209 turns the sampling LED 110 off. In some embodiments, the microcontroller 205 may take multiple samples and averages them to obtain a value for the fluorescent signal. However, the averaging will be completed before the sampling LED control signal 209 turns the sampling LED 110 on for the next cycle.

One useful feature of some embodiments is that the sample LED 110 and the detection circuitry can remain synchronized by using the same control signal. In the general use of the fluorometer, the sampling LED 110 sends a signal (the light) into the sample, and the sample's response to that light is measured. It is useful if the detection circuitry is set up so that it detects when the response is actually happening. So in some embodiments, the design circuitry uses only one signal, namely the sampling LED control signal 209, to control both the sampling LED 110 and the detection circuitry 290. With only one signal turning on both the sampling LED 110 and the detection circuitry 290 the whole system remains synchronized, which enhances the accuracy of the measurement. In alternate embodiments which use separate signals control the LED 110 and the analog switch 240, small differences in timing lead to significant measurement errors.

IV. Method for Measuring Photosynthesis Parameters

Figure 7:
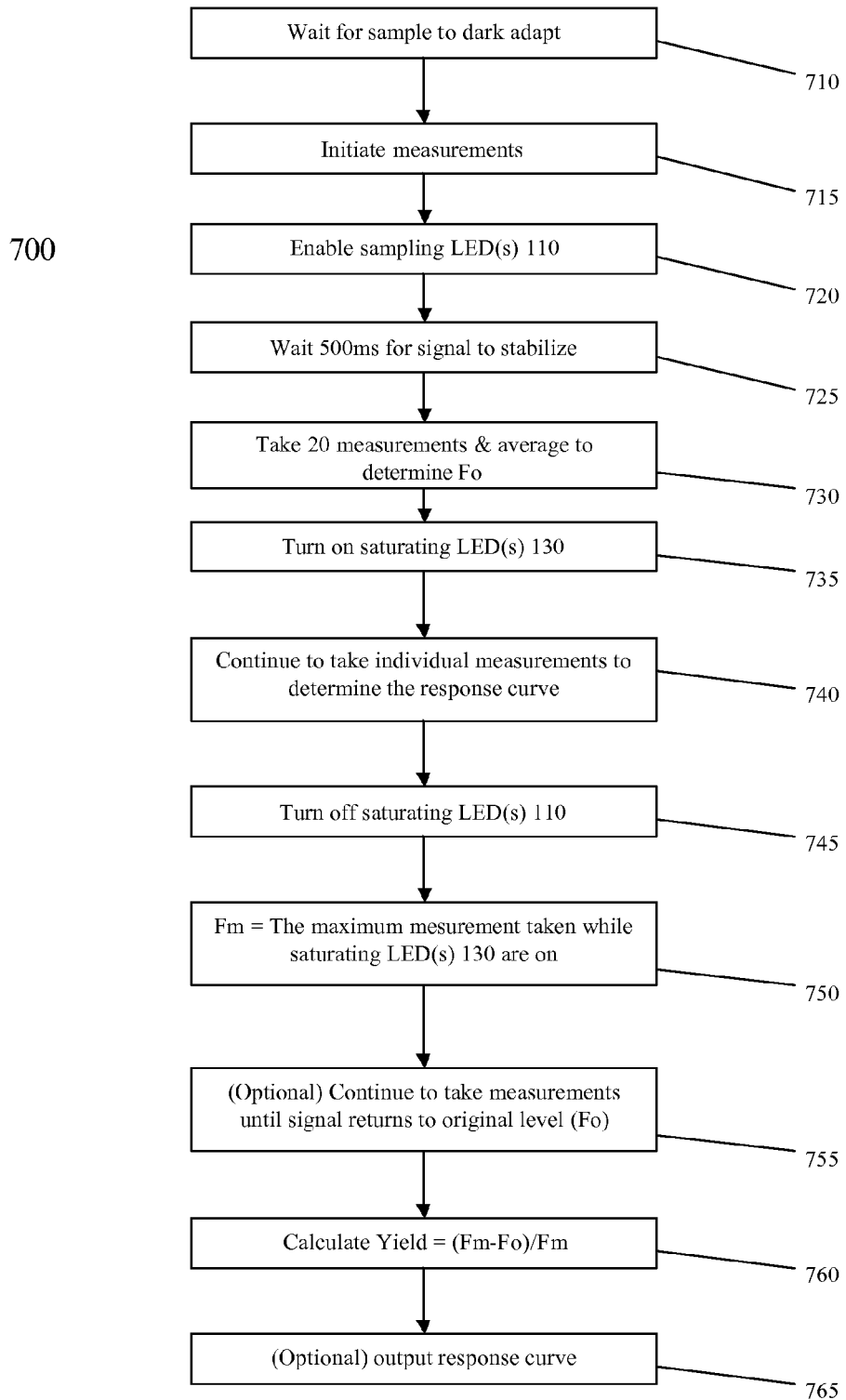
FIG. 7 illustrates a flow chart of the process to obtain information on the photosynthetic process.

FIG. 7 conceptually illustrates a typical process 700 performed by the microcontroller 205 to gather information on a photosynthetic process. This process is generally performed on a sample of water in which photosynthetic material is potentially present. Often this material would be some form of plant life, or other photosynthetic life, or bits of such life. As shown in this figure, the process begins by waiting (at 710) for a sample to "dark adapt". During this step, the sample is left in the dark for a period of time (anywhere from a few seconds to 10 minutes) so that very little photosynthesis is taking place. This causes the sample to fully utilize any light available for photosynthesis when it becomes available, which also gives a minimum fluorescent signal ("Fo").

In some embodiments, once the sample is dark adapted (at 710), the process is initiated (at 715) either by an external signal or at a pre-determined time. Sampling LED(s) 110 are enabled (at 720) and the system waits 500 ms for the signal to stabilize (at 725). The illumination by the sampling LED 110 causes the sample to fluoresce, the detection circuitry 290 then measures this fluorescence. A series of measurements are taken (at 730). The measurements are averaged. This average determines the minimum fluorescent value Fo. After obtaining (at 730) the minimum fluorescent value, the process turns on (at 735) the set of one or more saturating LEDs 130. The process leaves (at 740) the set of LEDs 130 on for some period of time while continuing to measure fluorescence using sampling LED 110. The photodiode 170 has a high enough dynamic range to distinguish between fluorescence caused by the sampling LED 110 and fluorescence caused by the saturating LED 130. In some embodiments, the process leaves the set of LEDs 130 on for one second. In other embodiments, the process leaves the one or more saturating LED 130 for a varying amount of time. Some embodiments allow a user to select the period of time for leaving "on" the saturating LED.

After leaving the one or more saturating LED(s) 130 on for a period of time, the process turns off (at 745) the one or more saturating LED(s) 130. In some embodiments, the process uses (at 750) the maximum fluorescent signal measured (at 740) to determine (Fm). After taking (at 750) the Fm, the process may continue to take (at 755) additional measurements of the fluorescent signal generated by the sample, using the sampling LED 110 to illuminate the sample. The illumination by the sampling LED 110 causes the sample to fluoresce, the detection circuitry 290 then detects this fluorescence. These measurements continue until the fluorescent signal returns to the Fo level, in some embodiments. Some embodiments use these additional measurements to determine other parameters of the photosynthetic process. Once the process measures the Fm, the process determines (at 760) a yield for the sample. The yield is defined as the difference between Fm and Fo divided by Fm. The yield is a measurement of the health of the living things in the water, a high yield indicates they are healthy, a low yield indicates they are unhealthy. The entire response curve may be stored or outputted (at 765) for further analysis or to determine additional parameters.

Figure 8:
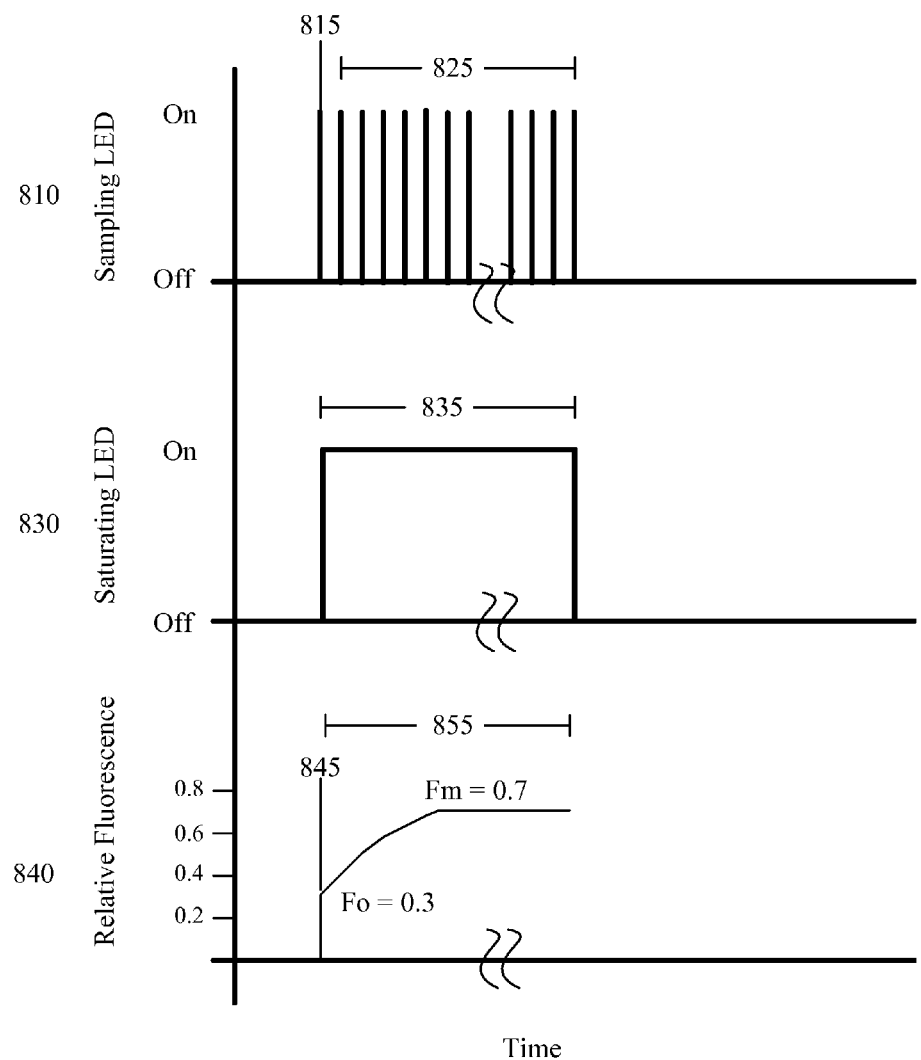
FIG. 8 illustrates a protocol for the fluorometer to determine certain parameters of the photosynthetic process.
Figure 9:
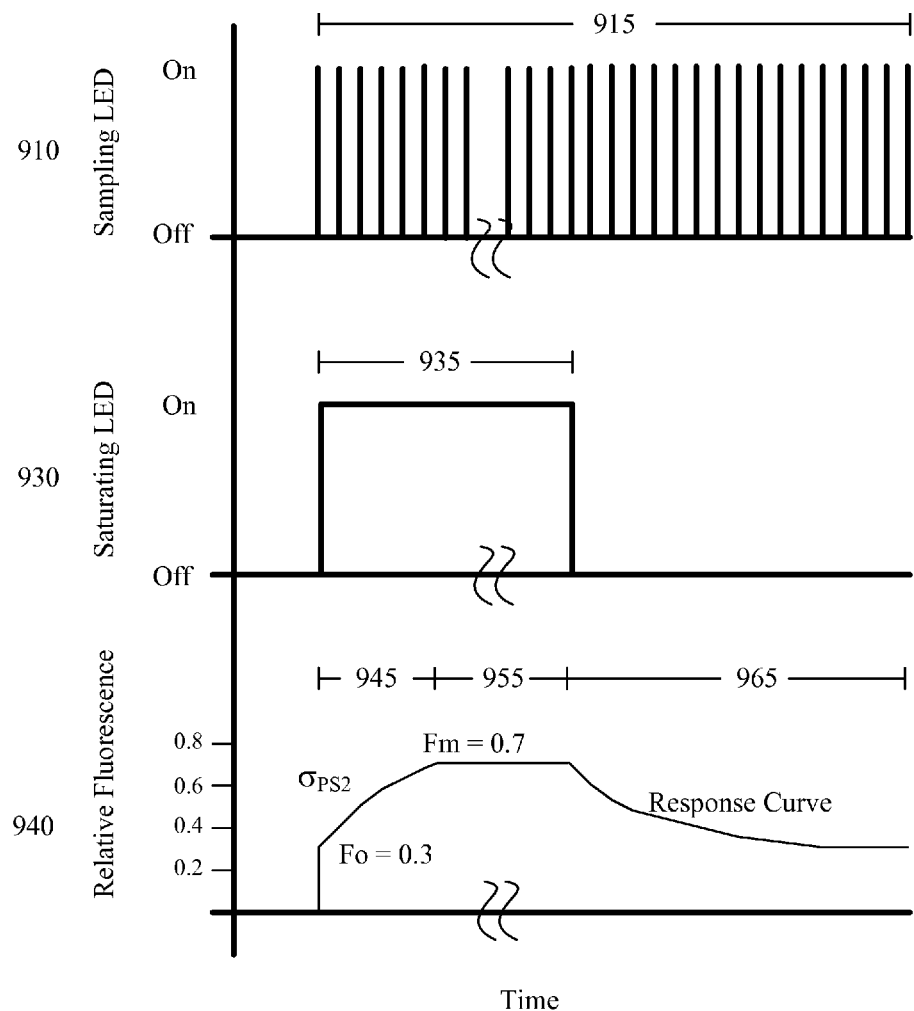
FIG. 9 illustrates another protocol for the fluorometer to determine certain parameters of the photosynthetic process.

The invention can be used to determine multiple parameters of the photosynthetic process. FIGS. 8 and 9 illustrate different protocols that can be used to determine an increasing number of parameters.

FIG. 8 illustrates a protocol that determines the yield of the photosynthetic process. This protocol involves dark adapting the sample as described above and taking one fluorescent measurement or averaging a series of fluorescent measurements to measure Fo, using the sampling LED 110 to illuminate the sample to obtain a minimum fluorescent value. The illumination by the sampling LED 110 causes the sample to fluoresce, the detection circuitry 290 then detects this fluorescence. Then saturating LED 130 is turned on for some period of time (e.g. 1 second) while continuing to take fluorescent measurements to obtain the maximum fluorescent value Fm. Variable fluorescence (Fv) is determined by subtracting Fo from Fm. Yield is determined by dividing Fv by Fm, giving a number between 0 and 1.

As shown in the figure, graph 810 of sampling LED 110 shows the "on" or "off" state of the sampling LED 110 (not shown in FIG. 8) versus time. The relative length of the periods of the saturating and sampling LEDs in the diagram may obscure the sequence of events, so the exact sequence will be described here. The spike 815 represents the sampling LED 110 being turned on for a brief time and then turned off just before saturating LED 130 is turned on. The sampling LED remains off until the first of spikes 825, which represent the sampling LED 110 being turned on for a brief time and then turned off for a longer period of time while saturating LED 130 is turned on.

Graph 830 of saturating LED 130 shows that saturating LED 130 has an "on" period 835 of some period, (e.g. one second). Graph 840 represents the relative fluorescence versus time. Section 845 represents the relative fluorescence while the saturating LED 130 is off. Section 855 represents the relative fluorescence while saturating LED 130 has been turned on.

Photosystem II (PS2) is part of the process of photosynthesis. FIG. 9 illustrates a protocol that determines the functional absorption cross-section of PS2 ($\sigma_{PS2}$) and the response curve of the sample. The protocol starts by duplicating the protocol of FIG. 8. Measuring the initial slope of this response gives a measurement of $\sigma_{PS2}$. In this protocol, measurements continue to be made after Fm has been measured. The measurements continue until the sample's fluorescent output diminishes back to its Fo value. The resulting response curve is another measure of the photosynthetic process. It is the prime measurement used in an instrument to protect natural water supplies against chemical or biological hazards as described by Miguel Rodriguiez, Jr. et. al. in the article *Sensors For Rapid Monitoring Of Primary-Source Drinking Water Using Naturally Occurring Photosynthesis* published in the Spring 2002 edition of the journal *Biosensors and Bioelectronics*.

By varying the combination of saturating pulse duration and intensity and sampling times, many protocols can be developed to measure additional parameters of the photosynthetic process. Examples of additional protocols can be found in Kolber III with further protocols likely to be developed as knowledge in the field expands.

As shown in the figure, graph 910 of sampling LED 110 shows the "on" or "off" state of the sampling LED 110 (not shown in FIG. 9) versus time. The spikes 915 represent the sampling LED 110 being turned on for a brief time and then turned off for a longer period of time.

Graph 930 of saturating LED 130 shows that saturating LED 130 has an "on" period 935 of some period, (e.g. one second). Graph 940 represents the Relative Fluorescence versus time. Section 945 represents the relative fluorescence while the saturating LED 130 is on and before the sample is saturated. Section 955 represents the relative fluorescence while the saturating LED 130 is on and after the sample is saturated. Section 965 represents the relative fluorescence after the saturating LED 130 has been turned off and the Sampling LED 110 continues to flash repeatedly until the relative fluorescence returns to Fo.

While different protocols have been described, one of ordinary skill in the art will recognize that many different protocols can be implemented using variations of timing of sampling LED(s) 110, timing of saturating LED(s) 130, and intensity of saturating LED(s) 130.

What is claimed is:

1. A submersible fluorometer for measuring a fluorescence of a photosynthetic material in a liquid, the fluorometer comprising:
   a) a set of light emitting diodes (LEDs) for supplying light to direct towards the liquid, wherein said set of LEDs is for providing light for both saturating the photosynthetic material in the liquid and sampling the fluorescence of the photosynthetic material;
   b) a photodiode for measuring a detected light emitted from the liquid, said detected light used for measuring said fluorescence of said photosynthetic material in the liquid; and
   c) a first water-tight volume for protecting said photodiode from the liquid.

2. The submersible fluorometer of claim 1, wherein said first water-tight volume contains a printed circuit board.

3. The submersible fluorometer of claim 1 further comprising a first set of at least one o-ring to seal said first water-tight volume.

4. The submersible fluorometer of claim 3 further comprising a second set of at least one o-ring to seal said first water-tight volume.

5. The submersible fluorometer of claim 1 further comprising a second water-tight volume containing a set of lenses.

6. The submersible fluorometer of claim 5, wherein said set of lenses comprises a lens for collimating light.

7. The submersible fluorometer of claim 1, wherein said set of light emitting diodes are in substantially a common plane.

8. The submersible fluorometer of claim 7, wherein said photodiode is aligned orthogonally to said common plane.

9. The submersible fluorometer of claim 1, wherein the set of light emitting diodes comprises a plurality of sampling light emitting diodes.

10. The submersible fluorometer of claim 1, wherein the set of light emitting diodes comprises a plurality of saturating light emitting diodes.

11. The submersible fluorometer of claim 1 further comprising an emission filter between said liquid and said photodiode.

12. The submersible fluorometer of claim 11 further comprising a lens for collimating light orthogonally to said emission filter.

13. The submersible fluorometer of claim 1, wherein said first water-tight compartment is for keeping said photodiode dry when said fluorometer is completely submerged in said liquid.

14. The submersible fluorometer of claim 1 further comprising an aperture for blocking a direct line of sight between said set of LEDs and said photodiode.

15. The submersible fluorometer of claim 1, wherein each LED of said set of LEDs is for providing light for both saturating the photosynthetic material in the liquid and sampling the fluorescence of the photosynthetic material.

16. The submersible fluorometer of claim 15, wherein said each LED of said set of LEDs is for providing different brightness levels to produce light for said saturating and light for said sampling.

17. A submersible fluorometer for measuring a fluorescence of a photosynthetic material in a liquid, the fluorometer comprising:
   a) a set of light emitting diodes (LEDs) for supplying light to direct towards the liquid;
   b) a photodiode for measuring a detected light emitted from the liquid, said detected light used for measuring said fluorescence of said photosynthetic material in the liquid;
   c) a first water-tight volume for protecting said photodiode from the liquid; and
   d) a second water-tight volume containing a printed circuit board.

18. The submersible fluorometer of claim 17, further comprising a plurality of o-rings to seal said first and second water-tight volumes.

19. A submersible fluorometer for measuring a fluorescence of a photosynthetic material in a liquid, the submersible fluorometer comprising:
   a) a set of sampling light emitting diodes for supplying a sampling excitation light to direct towards the liquid;
   b) a set of saturating light emitting diodes for supplying a saturating excitation light to direct towards the liquid;
   c) a photodiode for measuring a detected light emitted from the liquid in response to said sampling excitation light, said detected light used for measuring said fluorescence of said photosynthetic material in the liquid; and
   d) an endcap sealing off a water-tight volume.

20. The submersible fluorometer of claim 19, wherein said water-tight volume contains electronics.

21. The submersible fluorometer of claim 19 further comprising:
   a) a tubular housing for inserting said endcap; and
   b) a set of at least one o-ring, wherein said set of at least one o-ring provides a water-tight seal between said tube and said endcap.

22. The submersible fluorometer of claim 19, wherein said submersible fluorometer is functional at depths of 500 or more meters below a surface of water.

23. The submersible fluorometer of claim 19 further comprising a connector that screws into said endcap.

24. The submersible fluorometer of claim 19, wherein said submersible fluorometer measures fluorescence while said saturating LED is turned on.

25. A submersible fluorometer for measuring a fluorescence of a photosynthetic material in a liquid, the submersible fluorometer comprising:
   a) a set of sampling light emitting diodes for supplying a sampling excitation light to direct towards the liquid;
   b) a set of saturating light emitting diodes for supplying a saturating excitation light to direct towards the liquid;
   c) a photodiode for measuring a detected light emitted from the liquid in response to said sampling excitation light, said detected light used for measuring said fluorescence of said photosynthetic material in the liquid; and
   d) an optical head for holding a set of optics, wherein said optical head is for sealing off a water-tight volume.

26. The submersible fluorometer of claim 25 further comprising a set of o-rings around said optical head.

27. The submersible fluorometer of claim 25, wherein said set of optics comprises a collimating lens.

28. The submersible fluorometer of claim 25, wherein said set of optics comprises an emissions filter.

29. The submersible fluorometer of claim 25 further comprising an LED holder within said optical head.

30. A submersible fluorometer for measuring a fluorescence of a photosynthetic material in a liquid, the fluorometer comprising:

a) a sample chamber open to the liquid;
b) a photodiode for measuring a light from the sample chamber;
c) a transparent region of said sample chamber for allowing said light to reach said photodiode; and
d) a set of light emitting diodes (LEDs) for supplying light to the sample chamber, wherein the set of LEDs comprises a set of saturating LEDs for supplying light to said liquid and a set of sampling LEDs for triggering fluorescence of the photosynthetic material in the liquid.

31. The submersible fluorometer of claim 30, wherein the set of sampling LEDs and the set of saturating LEDs surround the sample chamber.

32. The submersible fluorometer of claim 30, wherein said sample chamber is surrounded by a transparent tube between said sample chamber and said set of LEDs.

* * * * *

UNITED STATES PATENT AND TRADEMARK OFFICE
CERTIFICATE OF CORRECTION

PATENT NO.       : 7,470,917 B1                                    Page 1 of 1
APPLICATION NO.  : 11/422064
DATED            : December 30, 2008
INVENTOR(S)      : Sang Hoang et al.

It is certified that error appears in the above-identified patent and that said Letters Patent is hereby corrected as shown below:

Title Page
Item (75), line 6 which reads "Frank Szcurko, Belmont, CA (US)" should read (after correction of a missing letter in the inventor's name) --Frank Szczurko, Belmont, CA (US)--.

Signed and Sealed this

Fifth Day of January, 2010

David J. Kappos
*Director of the United States Patent and Trademark Office*